(12) United States Patent  
Usowicz et al.

(10) Patent No.: US 7,596,988 B2  
(45) Date of Patent: Oct. 6, 2009

(54) HIGH PERFORMANCE LIQUID CHROMATOGRAPHY SAMPLE INTRODUCTION OPTIMIZED WITH BUBBLE DETECTION

(75) Inventors: James E. Usowicz, Webster, MA (US); Peyton C. Beals, Wrentham, MA (US); Russell Keene, Sudbury, MA (US); Richard Kent, Norfolk, MA (US); Miguel Soares, Norton, MA (US); John Heden, Hollis, NH (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 10/598,071

(22) PCT Filed: Mar. 2, 2005

(86) PCT No.: PCT/US2005/006719  
§ 371 (c)(1),  
(2), (4) Date: Mar. 30, 2007

(87) PCT Pub. No.: WO2005/091936  
PCT Pub. Date: Oct. 6, 2005

(65) Prior Publication Data  
US 2007/0287192 A1    Dec. 13, 2007

Related U.S. Application Data

(60) Provisional application No. 60/550,971, filed on Mar. 5, 2004.

(51) Int. Cl.  
*G01N 30/28* (2006.01)  
*G01N 30/32* (2006.01)

(52) U.S. Cl. .............. 73/61.52; 73/61.55; 73/61.56; 73/61.57; 210/635; 422/70

(58) Field of Classification Search ............... 73/61.43, 73/61.52, 61.53, 61.55, 61.56, 61.57, 61.58, 73/61.59, 61.61; 210/635, 656; 422/69, 422/70; 436/161; 585/825  
See application file for complete search history.

(56) References Cited

U.S. PATENT DOCUMENTS 4,117,727 A    10/1978    Friswell et al.

(Continued)

FOREIGN PATENT DOCUMENTS

JP    60243562 A  *  12/1985

(Continued)

*Primary Examiner*—David A. Rogers  
(74) *Attorney, Agent, or Firm*—Jamie H. Rose; Anthony J. Janiuk

(57) ABSTRACT

A device (100) for detecting a condition in a fluid system (14) and initiating a response based on the condition. The device consists of a sensor (12) that responds to a first and second condition of the fluid (13) in the system and a control means (10) that receives the responses and generates command signals in based on the received response. In a liquid chromatography system, the device is used to determine the volume of components of the fluid system. In addition, the device allow leaks to be detected and permits the fluid in the system to be transported at a optimum speed. The device is well implemented utilizing to a light emitter and light receptor that are sensitive to the fluid in either a gaseous or liquid state.

34 Claims, 8 Drawing Sheets

U.S. PATENT DOCUMENTS

| | | |
|---|---|---|
| 4,802,981 A | 2/1989 | Kenney et al. |
| 4,939,943 A | 7/1990 | Stromeier et al. |
| 5,004,538 A | 4/1991 | Apfel |
| 5,083,862 A * | 1/1992 | Rusnak ............ 356/239.1 |
| 5,112,492 A | 5/1992 | Ransohoff |
| 5,129,415 A | 7/1992 | Runyon et al. |
| 5,242,586 A | 9/1993 | Ransohoff et al. |
| 5,316,179 A | 5/1994 | Ioannides et al. |
| 5,393,434 A | 2/1995 | Hutchins et al. |
| 5,823,747 A * | 10/1998 | Ciavarini et al. ............ 417/216 |
| 5,960,129 A * | 9/1999 | Kleinschmitt ................ 385/12 |
| RE37,553 E | 2/2002 | Ciavarini et al. |

FOREIGN PATENT DOCUMENTS

| | | |
|---|---|---|
| JP | 403223671 | 10/1991 |
| JP | 406273403 | 10/1994 |
| JP | 407005157 | 1/1995 |
| JP | 2002267644 A * | 9/2002 |

* cited by examiner

HIGH PERFORMANCE LIQUID CHROMATOGRAPHY SAMPLE INTRODUCTION OPTIMIZED WITH BUBBLE DETECTION

CROSS REFERENCE TO RELATED APPLICATIONS

This application claims priority from U.S. Provisional patent Application No. 60/550,971, filed Mar. 5, 2004. The contents of these applications are incorporated herein by reference.

STATEMENT ON FEDERALLY SPONSORED RESEARCH

N/A

FIELD OF THE INVENTION

The present invention is directed to a device for identifying a condition in a fluid system and initiating a response thereto.

BACKGROUND OF THE INVENTION

The size of samples being analyzed by liquid chromatography has been decreasing. The need to segregate and handle smaller sample volumes and to control the position of the sample in the face of higher pressures and leakage has increased. One area where this is especially important is in the sample injector portion of an in-line liquid chromatography instrument. In-line operation of a liquid chromatograph involves automated selection of samples that are sequentially drawn into a needle or capillary and then loaded into a sample loop by pulling the fluid through the needle and any associated tubes and valves into the sample loop. After the sample is in the sample loop, the sample loop is connected to an injection mechanism, such as a pump/detector system, that pushes the sample through a liquid chromatography column where the separation takes place. The sample can be pulled through the system of tubes at a flow rate that is directly related to the vapor pressure of the fluid. If the fluid is drawn through the tubing too quickly, the fluid can vaporize and cause undesirable effects on sample integrity as well as sample positioning within the sample loop. With in-line operation however, the vapor pressure of the samples can vary. Currently the drawing mechanism has to be set to a speed that will handle all the anticipated samples. It would be advantageous to transport fluid at the optimum speed even when the viscosity of the fluid changes within a sequence of fluids.

Liquids that are drawn through a fluid path encounter friction at the walls of the tubes making up the fluid path. This causes some mixing of the liquids as the friction drags at the liquid next to the walls. When a sample bracketed by air gaps, as is known in the industry, passes through a fluid path, some of the liquid ahead of the bracketed sample transfers across the air gap causing the volume of fluid ahead of the sample to change. As the diameter of the fluid path decreases, this change in volume causes an inaccuracy in positioning of the samples.

All of the components of the injector are replaceable and must be cleaned between injections. Because there are many joints and connections, there is an opportunity for leaks to develop. These leaks may be small enough that they evaporate before they can be visually detected. However, the leakage will degrade the accuracy of the injection by causing undesirable sample movement. Early detection of such leaks would allow scheduled replacement of parts and improve the quality of the operation of the instrument.

A further consequence of the replaceable components utilized in the injector is the inaccuracy that accrues due to the tolerance of the components. In general, components such as an aspirating needle and a sample loop have an internal volume manufactured to a tolerance that is not as precise as desired. While the internal volumes are manufactured to fall within a predetermined range, the range is too broad to assure accurate positioning of a sample within the sample loop. As the parts are replaced, the control mechanism cannot use small volumes of sample because it cannot be sure of the volume taken up by the needle and/or where that volume is positioned in the sample loop. The volume of the replacement part is not specified with sufficient precision to allow the sample to be positioned in the sample loop accurately. The tolerance problem especially effects partial loop injections.

The systems can suffer from changes in volume that impede accuracy. Deposits that build up in the tubing change the volume of the system, can create turbulence within the tubing and therefore degrade performance. The variability of the volume of these components makes it hard to minimize the amount of sample being used while providing a precise amount of sample to the column.

Each of these problems and challenges of handling small volumes of sample point to a need for a device that provides more information about the fluid system.

SUMMARY OF THE INVENTION

The present invention is directed to a device for identifying a condition in a fluid system and initiating a response thereto. The device comprises a sensor for placement in communication with a fluid in the fluid path of the fluid system and a control means for receiving the outputs of the sensor. The sensor outputs a first signal in response to a first condition of the fluid and a second signal in response to a second condition of the fluid. After the control means receives either the first or second signal, it sends at least one command signal to initiate a response that is based on the received signals.

In one embodiment, fluid, in a gaseous state, corresponds to the first condition and fluid, in a liquid state, corresponds to the second condition. When utilized, the device is incorporated in a fluid system. This embodiment is useful for determining when fluid systems have approached conditions in which the fluids are assuming the gaseous state.

Preferably, the fluid system comprises a fluid conduit having an input end and an output end that is connected to a fluid movement means for moving an aliquot of fluid. The fluid movement means, preferably a metering syringe, is responsive to a fluid movement command signal. A representative fluid system is a liquid chromatography system and in particular, the sample injector of a liquid chromatography system.

In one embodiment, the sensor is placed between the fluid movement means and the output end of the fluid conduit. The control means issues at least one fluid movement command signal that causes the fluid movement means to draw fluid in through the input end at a initial rate. The control means issues fluid movement command signals that increase the rate as long as it is receiving the second signal. When the control means receives a first signal, indicating gas at the sensor, it issues fluid movement command signals that reduce the rate. This embodiment moves the fluid at an optimum rate that that prevents vaporization of the fluid. When the device is operated to prevent fluid in a gaseous state from passing the sensor, the control means stops issuing fluid movement command signals upon receiving a first signal.

Preferably, the fluid system further comprises positioning means for moving the input end between at least one source of liquid and at least one source of gas. The positioning means is responsive to a position command signal to move the input end. The control means determines the volume of the fluid path by measuring the volume of fluid it will hold. To do this, it issues fluid movement and position command signals to either draw an aliquot of gas from the gas source into the system and then counts the number of aliquots of liquid drawn into the fluid path until it receives the first signal or fills the fluid path with liquid and then draws in gas until a first signal is received. The control means multiplies the volume of an aliquot of fluid by the counted number of aliquots moved to determine the volume of the fluid path.

Preferably, the control means determines the volume of the fluid conduit and compares that volume to a control value to detect a reduction in the volume of the fluid conduit. This reduction in the volume is indicative of an obstruction. Preferably the control value is selected from a value of the volume of a previously measured, an average of previous values of the volume or a predetermined value.

Preferably, the fluid path further includes an aspirating needle connected to the input end. Preferably, the fluid path also comprises a valve means disposed between the aspirating needle and the input end. The valve means has a plurality of positions wherein fluid is allowed to flow between various ports. The valve means is responsive to a valve command signal to assume one of the positions. The control means determines the volume of the fluid path of the needled system in the manner described above. Further, when the volume of the valve is known, the control means determines the volume of the aspirating needle by subtracting the valve volume and the volume of the fluid conduit from the volume of the needled system.

In a preferred embodiment, the fluid path has a sample loop in communication with the valve means. One of the positions of the valve means is a loop position wherein fluid flows through the sample loop and through the valve means. The valve means assumes the loop position in response to the valve command signal. The control means calibrates the volume of a sample loop by determining the difference in volume between the fluid system with and without the sample loop engaged. When one of the sources of fluid is a source of sample liquid, the control means sends command signals to the positioning means, valve means and fluid movement means to place a gas bubble in front of a quantity of sample liquid. One way to position the sample in the sample loop is to have the control means move the fluids until the receipt of a first signal indicates that the gas bubble has exited the sample loop and the sample fluid is positioned in the loop.

In a further embodiment, the fluid system further comprises a pressurizing means connected to the source of liquid. The pressurizing means is responsive to a pressurize command signal to apply a predetermined pressure to the source of liquid. The control means sends command signals to the positioning means, valve means, fluid movement means and pressurizing means to fill the fluid path with liquid with a gaseous region of a known number of aliquots of gas in the fluid near the aspirating needle tip. The volume of the liquid, in front of the gas, is determined before pressurization and after pressurization. A change in volume after the fluid system has been held at an elevated pressure is indicative of a leak in the fluid system. The control means determines a compliance factor of the fluid system by determining the difference in volume of the fluid system when it is at ambient pressure and when it is at an elevated pressure.

Preferably, the fluid system further comprises a sealing means. The sealing means is operative to seal the input end when the positioning means positions the input end against the sealing means in response to position command signal. With the fluid path sealed, the control means creates a reduced pressure in the fluid system by removing some fluid from the sealed system. The reduced pressure pulls air into the fluid path through any leaks and allows the control means to determine a leak rate from a change in volume of the gaseous region in the fluid path after the system has been under reduced pressure for a time.

In a preferred embodiment, the sensor of the device comprises a light emitter and a light receptor. The light emitter is constructed and arranged to emit light through the fluid. The light emitter produces a beam of light, which, after traveling through the fluid, has a first characteristic in the presence of a liquid and a second characteristic in the presence of a gas. The light receptor is constructed and arranged to receive light from the fluid. The light receptor produces the first signal in response to light having the first characteristic and the second signal in response to light having the second characteristic. When the control means receives these signals, it distinguishes the presence of gas or liquid in the fluid system. The device functions in a fluid system that comprises at least one vessel containing the fluid that has at least one wall with a transparent portion. The sensor communicates with the fluid through the transparent portion of the vessel. One implementation of the vessel is a tube that is transparent. The sensor is position so that the light emitter is constructed and arranged to pass light into the tube through the transparent portion and the light receptor is constructed and arranged to receive light from the tube through the transparent portion. Such a sensor may be used to detect bubbles.

One embodiment of the present invention is a method of monitoring fluid in a fluid system. The fluid system has a fluid path comprised of a fluid conduit having an input end and an output end and has a fluid movement means for moving an aliquot of fluid. The fluid movement means is responsive to a fluid movement command signal. The method comprises providing a sensor and a control means. The sensor is for placement in communication with the fluid in the fluid system. The sensor outputs a first signal in response to the fluid being in a gaseous state and a second signal in response to the fluid being in a liquid state. The control means is for receiving the first signal and the second signal and for sending at least one command signal for initiating a response based on the received signals. The sensor is placed in communication with the fluid between the fluid movement means and output end of the fluid conduit. The control means is connected to send a fluid movement command signal to the fluid movement means. The control means issues fluid movement command signals to cause the fluid movement means to draw fluid in through the input end at an initial rate.

Preferably, the method is used to move liquid at an optimum rate that prevents vaporization. The control means issues fluid movement command signals that increase the rate while receiving the second signal and issues fluid movement command signals that decrease the rate while receiving the first signal. Alternatively, the method can be used to prevent fluid in a gaseous state from passing the sensor. Then, the control means stops issuing fluid movement command signals to the fluid movement means upon receiving the first signal.

The method is used to determine the volume of the fluid path when the fluid system further comprises a positioning means for moving the input end between a source of liquid and a source of gas. The positioning means is responsive to a position command signal to move the input end. The position command signal is connected between the control means and the positioning means. The control means commands the fluid system that has a fluid path full of liquid to draw an aliquot of gas from the source of gas. The control means then commands the fluid system to draw and count a plurality of aliquots of liquid from the source of liquid until the first signal is received by the control means. The control means determines the volume of the fluid path by multiplying the volume of an aliquot by the counted number of aliquots of fluid drawn.

Alternatively, the control means commands the fluid system that has a fluid path full of liquid to draw aliquots of gas from the source of gas until the first signal is received. By counting the aliquots moved, the control means determines the volume of fluid path in the same manner as above.

Preferably, the volume determining method is used for detecting an obstruction in the fluid system. An obstruction reduces the volume of the fluid system. The method compares the volume of the fluid conduit to a control value and identifies an obstruction when the volume is less than the control value.

Preferably, the fluid system further comprises an aspirating needle connected to the input end. The method determines the fluid comprising the volume of the aspirating needle and the fluid conduit. When the fluid system comprises a valve means disposed between the aspirating needle and the input end, the volume determining method determines a fluid path volume for the aspirating needle, fluid conduit and valve means combination. Such a valve means has a plurality of positions wherein fluid is allowed to flow between various ports. The valve means is responsive to a valve command signal to assume one of the positions. The method determines the aspirating needle volume by subtracting a valve volume and a fluid conduit volume from the combination volume.

The method is applicable to a fluid system that further comprises a sample loop in communication with the valve means. The valve means further has a loop position wherein fluid is allowed to flow through the sample loop and through the valve means. The valve means is further responsive to the valve command signal to assume the loop position. The method for finding volume is applied to determine the volume of the sample loop. Here, the control means determines an open position volume of the fluid path with the valve means in the open position. Then, the control means determines a loop position volume of the fluid path with the valve means in the loop position. Finally, the control means determines the loop volume by subtracting the open position volume from the loop position volume.

Preferably the device is used in a method to position liquid in the sample loop. The control means commands the valve means to assume the loop position and then draws an aliquot of gas from a source of gas into the fluid system. The control means then moves the input end to a source of fluid and draws a plurality of aliquots of liquid from the source of liquid until the first signal is received by the control means.

An alternate method to position liquid in the sample loop uses the volumes measured using the sensor to precisely determine how much fluid volume needs to be displaced to move a sample to a predetermined position in the sample loop. Once this volume is determined, the control means can move the sample at optimum speed and repeatedly position the sample precisely. This method is further refined to account for the effects of variations in pressure on the volume of fluid to be displaced.

When the fluid system further comprises a pressurizing means that is responsive to a pressurize command signal to apply a predetermined pressure on a source of liquid, the control means can determine a compliance factor of the fluid system. The method involves determining an ambient volume of the fluid system with ambient pressure on the fluid source and then determining a pressurized volume of the fluid system with a predetermined elevated pressure applied to the fluid source. The difference between these volumes is a compliance rate volume.

The pressurizing means is also used in the method for determining a leakage rate at a pressure. The control means draws a predetermined volume of gas into the fluid system forming known volume of liquid followed by a gas bubble in the fluid system. The control means places the input end in a source of liquid and issues a pressurize command to place the fluid system under elevated pressure. The control means waits a predetermined length of time before measuring the change in volume of the liquid in the system. Any decrease in volume beyond the decrease attributable to the compliance rate volume during a measured time is converted to a leak rate.

When a sealing means is part of the fluid system, a method of measuring the leak rate uses it. The sealing means is operative to seal the input end when the positioning means positions the input end against the sealing means. The method has the control means draw a predetermined plurality of aliquots of gas into the fluid system. The gas is followed by a number of aliquots of fluid forming a gas bubble in the fluid. The control means then seals the input end. When a number of aliquots of fluid are drawn from the system by the fluid movement means under control of the control means, a negative pressure is created. The control means maintains the negative pressure for a predetermined length of time. Any increase in volume of the gas bubble after a return to ambient pressure is indicative of a leak that has a calculable leak rate.

The methods above are well adapted to a device in which the sensor comprises a light emitter and a light receptor. The light emitter is constructed and arranged to emit light through the fluid. The light emitter produces a beam of light, which, after traveling through the fluid, has a first characteristic in the presence of a liquid and a second characteristic in the presence of a gas. The light receptor is constructed and arranged to receive light from the fluid. The light receptor produces the first signal in response to light having the first characteristic and the second signal in response to light having the second characteristic. When the control means receives these signals, it distinguishes the presence of gas or liquid in the fluid system. The device functions in a fluid system that comprises at least one vessel containing the fluid that has at least one wall with a transparent portion. The sensor communicates with the fluid through the transparent portion of the vessel. One implementation of the vessel is a tube that is transparent. The sensor is positioned so that the light emitter is constructed and arranged to pass light into the tube through the transparent portion and the light receptor is constructed and arranged to receive light from the tube through the transparent portion. The sensor is applicable to a fluid system such as a liquid chromatography system and an injector for a liquid chromatography system.

DESCRIPTION OF THE DRAWINGS

The above noted and other features of the invention will be better understood from the following detailed description, when considered in connection with the accompanying drawings, in which.

DETAILED DESCRIPTION

The present invention will be more fully illustrated by reference to the definitions set forth below.

As used herein, the term "leak" refers to a hole, mismatch of interconnecting components, crack or opening through which fluid escapes in a manner not intended by the user. The leak may be totally internal. That is, the fluid escapes from an area of high pressure to an area of low pressure within the apparatus. Or, such leak may be external, allowing fluid to escape from the confines of the hydraulic path. In a system utilizing small diameter components, such a leak from the system may evaporate before becoming visible.

A gas bubble sensor—can be implemented as liquid sensing light emitting diode/receiver but can also be piezo-electric devices or ultrasonic devices sensitive to gas or liquid in a system. The output of the gas bubble sensor, representing the state of the fluid being monitored, may be two signals—one for each possible state, an analog signal that assumes one of two values that is digitized before being input to a control means, a digitized representation of the state of the fluid or other means to represent two values.

As used herein, "pressure monitor" comprises any device for measuring pressure, including strain gauges and pressure transducers. The output of the pressure monitor, representing a measured pressure, may be an analog signal that is digitized before being input to a control means or may be a digitized representation of the measured pressure.

Valves are devices for closing, opening or directing fluid flow. Typical valves include mechanical check valves and active valves. Mechanical check valves are responsive to pressure. Active valves receive a signal, which directs power means, such as motors, solenoids and the like, to open or close the valve. Cycling valves are capable of selectively opening and closing the flow of fluid from one or more sources or directing the flow to one or more destinations.

As used herein, the term "control means" means any processing entity that can receive information signals and send command signals. An embedded microprocessor with memory and an associated input/output section for signal handling is one implementation. Alternately, one of the central processors embedded in an instrument may act as the control means with the memory and input/output sections handling instrument as well as the device functions. Other central processors, as are known to those skilled in the art, can serve as the control means.

Figure 1B:
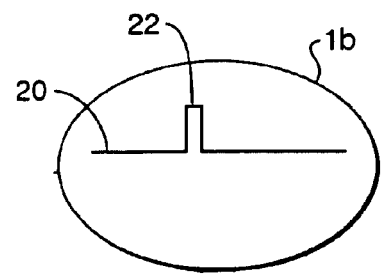
FIG. 1B illustrates a signal between the parts of the device of FIG. 1A.
Figure 1A:
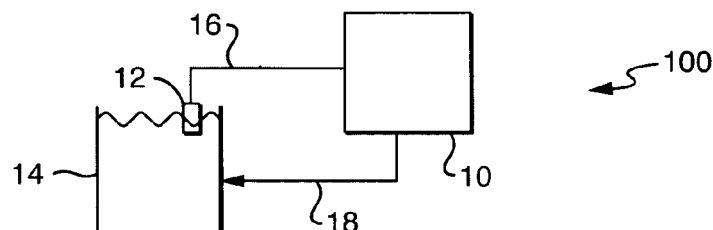
FIG. 1A illustrates an embodiment of the inventive device.

The present invention is directed to a device for identifying a condition in a fluid system and initiating a response thereto. The device 100, as depicted in FIG. 1A, comprises a sensor 12 for placement in communication with a fluid in the fluid system 14 and a control means 10 for receiving the outputs 16 of the sensor 12. As shown in FIG. 1B, the sensor 12 outputs a first signal 20 in response to a first condition of the fluid and a second signal 22 in response to a second condition of the fluid. After the control means 10 receives either the first or second signal, it sends at least one command signal 18 to initiate a response that is based on the received signals.

Figure 2:
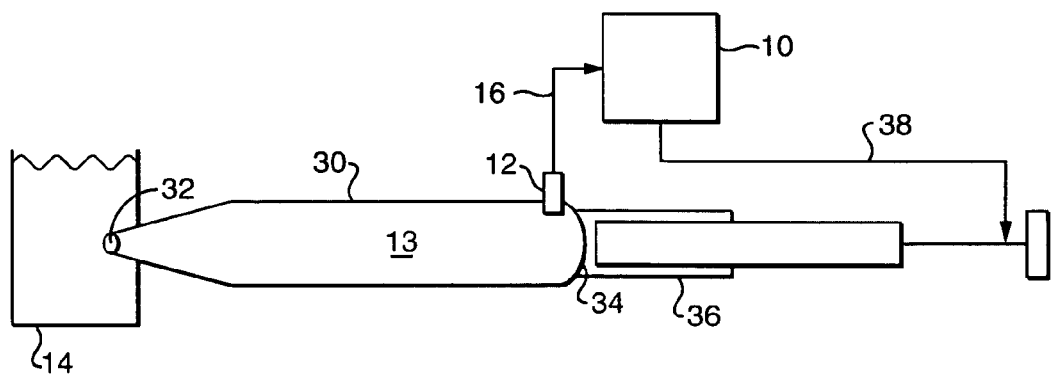
FIG. 2 illustrates the device of FIG. 1A disposed with a fluid system.

Preferably, the first condition is that the fluid is in a gaseous state and the second condition is that the fluid is in a liquid state. When utilized, the device is incorporated in a fluid system. Turning now to FIG. 2, one target fluid system comprises a fluid conduit 30 having an input end 32 and an output end 34 that is connected to a fluid movement means 36 for moving an aliquot of fluid. The fluid movement means 36, preferably a metering syringe, is responsive to a fluid movement command signal 38. A representative fluid system is a liquid chromatography system and in particular, the sample injector of a liquid chromatography system.

Preferably, the sensor 12 is placed between the fluid movement means 36 and the output end 34 of the fluid conduit. The control means 10 issues at least one fluid movement command signal 38 that causes the fluid movement means 36 to draw fluid in through the input end 32 at a initial rate. The control means 10 issues fluid movement command signals 38 that increase the rate as long as it is receiving the second signal indicating that the fluid remains a liquid. When the control means 10 receives a first signal, indicating that the fluid at the sensor is in the gaseous state, it issues fluid movement command signals 38 that reduce the rate. This embodiment moves the fluid at an optimum rate that prevents vaporization of the fluid. The same configuration is applicable to being operated to prevent fluid in a gaseous state from passing the sensor. In this case, the control means 10 stops issuing fluid movement command signals 38 upon receiving a first signal indicating gaseous fluid at the sensor 10.

Figure 3:
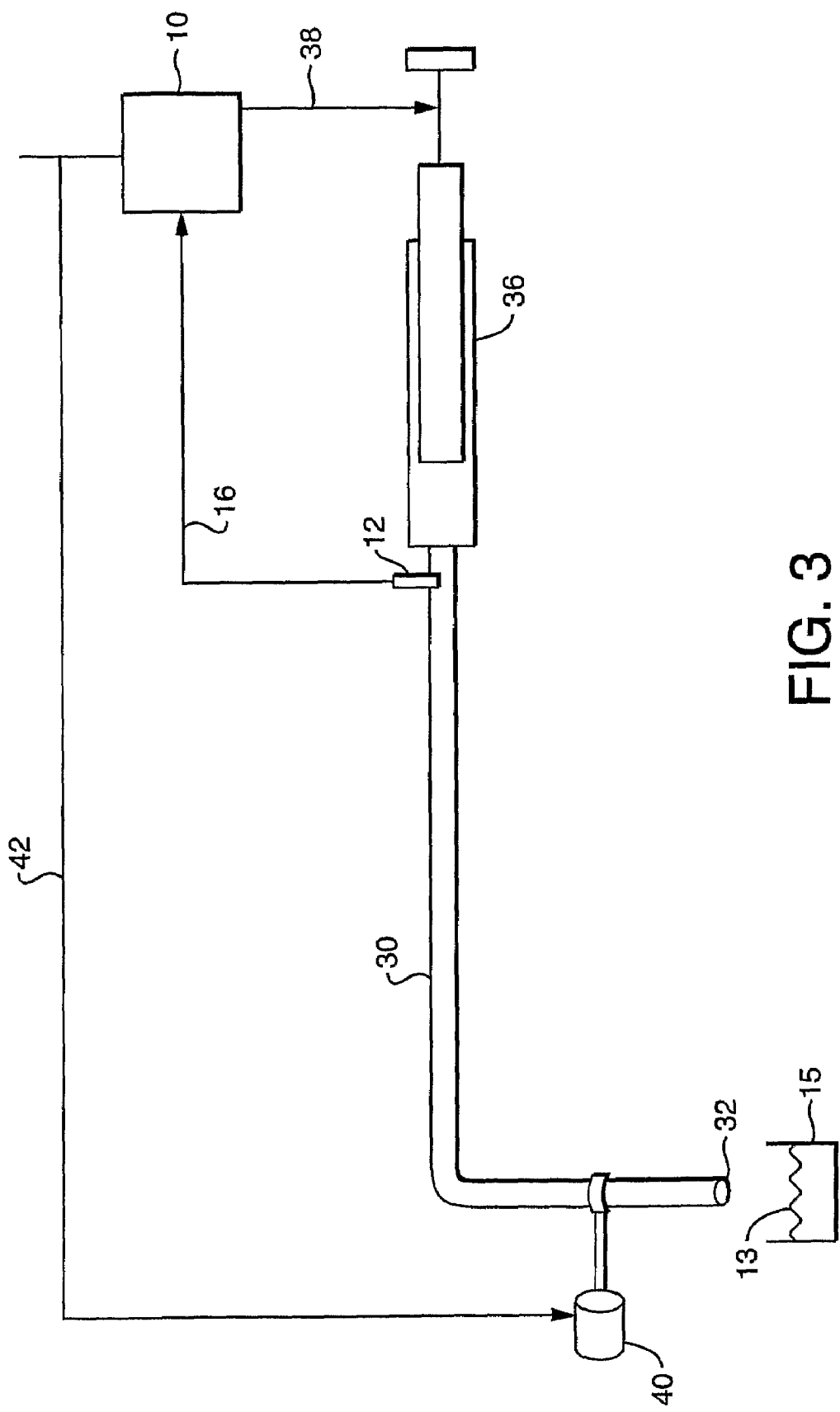
FIG. 3 illustrates the device of FIG. 1A disposed with another fluid system.

Another fluid system, illustrated in FIG. 3, is comprised of a fluid conduit 30 and fluid movement means 36 as above and also a positioning means 40 for moving the input end 32 between at least one source of liquid, such as liquid reservoir 15, and at least one source of gas, such as the free air. The positioning means 40 is responsive to a position command signal 42 to move the input end 32. The control means 10 can determine the volume of the fluid path, here the fluid conduit 30, by measuring the volume of fluid the fluid path will hold. To do this, the control means issues position command signals 42 to place the input end 32 in the gas source and issues fluid movement signals 38 to draw at least an aliquot of gas from the gas source into the fluid conduit 30. It then issues position command signals 42 to place the input end 32 in the liquid source 15, and issues fluid movement signals 38 to draw a counted number of aliquots of liquid into the fluid conduit 30 until it receives the first signal indicating that the gas bubble has reached the sensor 12. The control means multiplies the volume of an aliquot of fluid by the counted number of aliquots to determine the volume of the fluid conduit.

Alternately, the control means issues position command signals 42 to place the input end 32 in the liquid source 15 and issues fluid movement signals 38 to fill the entire fluid path with liquid. It then issues position command signals 42 to place the input end 32 in a gas source or free air. The control means issues fluid movement signals 38 to draw aliquots of gas into the fluid path while counting the aliquots moved.

When the control means receives the first signal, indicating that the gas has reached the sensor, it stops drawing in gas. The volume of the fluid path is determined by equation (1), where $$V_{BT} = V_a \cdot \#A \quad (1)$$

$V_{BT}$ is the volume of the fluid path to the sensor, $V_a$ is the volume of an aliquot of fluid and #A is the number of aliquots counted in moving the fluid until the first signal is received.

The measured value of the volume of the fluid conduit 30 can be retained by the control means 10 as a control value. When the control means 10 later determines the volume of the fluid conduit 30 and compares that volume to the control value, it is able to detect a reduction in the volume of the fluid conduit 30, which can be indicative of an obstruction. The control value may be a previous value of the volume, an average of previous values of the volume or a predetermined value.

Figure 4:
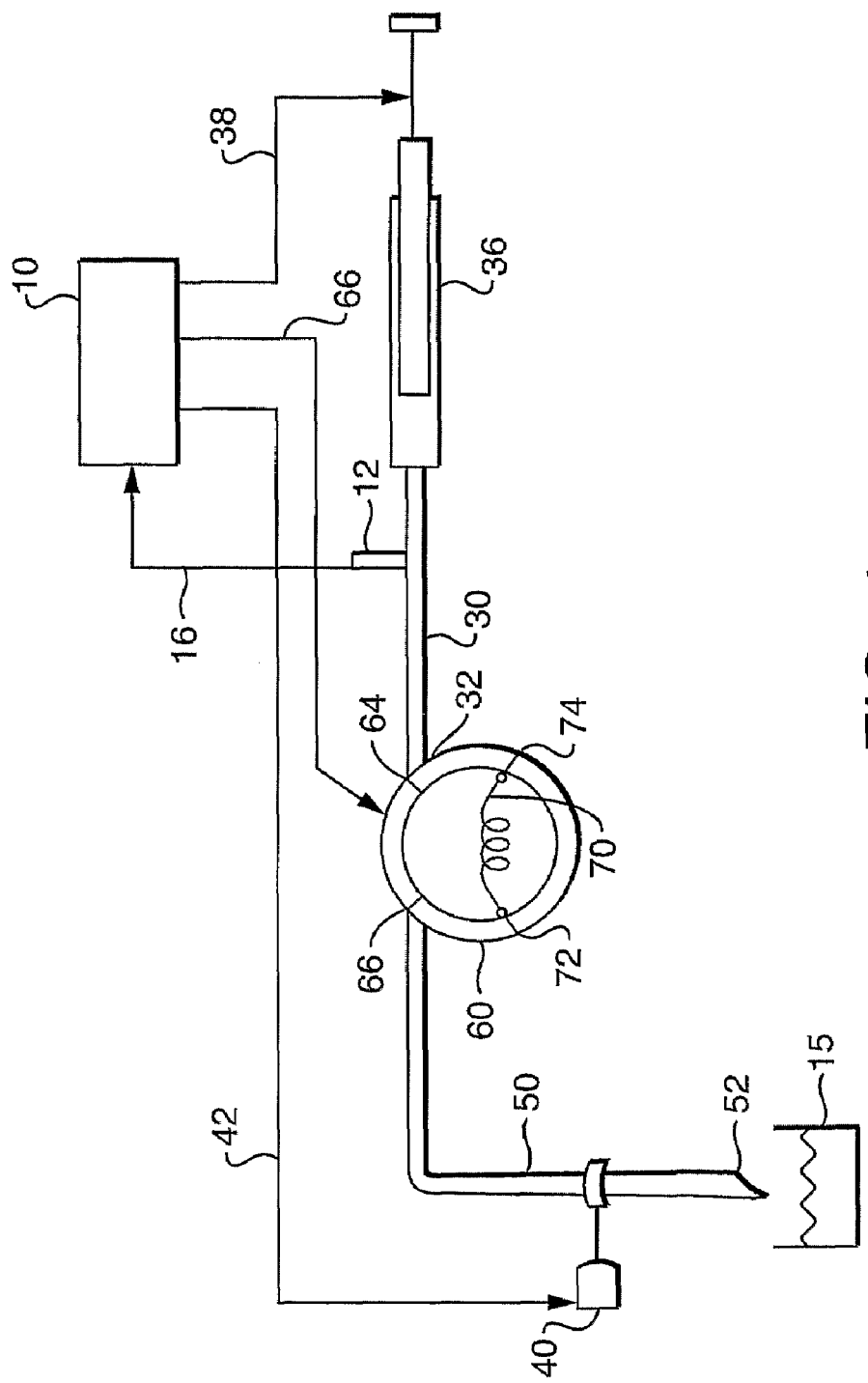
FIG. 4 illustrates the device of FIG. 1A disposed with a further fluid system.

In one embodiment, the fluid system further includes an aspirating needle 50 connected to the input end 32. Preferably, as shown in FIG. 4, the fluid system also comprises a valve means 60 disposed between the aspirating needle 50 and the input end 32. The valve means 60 has a first open position wherein fluid is allowed to flow from port one 62 to port two 64 through the valve means 60. The valve means 60 is responsive to a valve command signal 66 to assume a position. The control means 10 determines the volume of the fluid path of the needled system by placing the valve means in the first open position and issuing the required valve command signals 66 so that fluid flows between a first port 62 and a second port 64. Further, when the volume of the valve means 60 is known and the volume of the fluid conduit 30 is known from a prior measurement, the control means 10 determines the volume of the aspirating needle 50 by subtracting the valve volume and the volume of the fluid conduit 30 from the volume of the needled system. The equation for the needle volume is:

$$V_{NEEDLE} = V_{SYS} - V_{IV} - V_{BT} \quad (2)$$

Where $V_{SYS}$ the volume of the system, $V_{IV}$ is the internal volume of the valve, and $V_{BT}$ is the volume of the fluid path from the valve port to the sensor. Such a volume calculation is typically performed when a new aspirating needle 50 replaces an existing one because aspirating needle volumes are not specified with great accuracy.

In a preferred embodiment, the valve means 60 has a sample loop 70 disposed between two further ports 72, 74 of the valve means 60. The valve means 60 further has a loop position wherein fluid flows in through port 62, through the valve means to port 72, through the sample loop 70 to port 74 and through the valve means to port 64 and. The valve means 60 assumes the loop position in response to the valve command signal 66. The configuration of the device 100 and fluid system with sample loop 70 is used to place a known type of fluid in the sample loop 70. The control means 10 sends command signals to the positioning means 40, valve means 60 and fluid movement means 36 to place a gas bubble in front of a quantity of the specified liquid. The control means 10 sends command signals that move the fluids until the receipt of a first signal indicates that the gas bubble has exited the sample loop 70 and valve means 60 and the specified fluid is positioned in the sample loop 60.

Sample loops are changeable so that the sample loop volume is appropriately sized for the specified volume of sample to be injected into the chromatograph. However, the volume of many sample loops is specified only to within ±30%. More sample can be conserved and the control means 10 can assure that the sample loop 70 is fully filled, if the volume of the sample loop 70 is more precisely known. When a sample loop 70 is changed, the control means 10 calibrates the volume of a sample loop 70 by determining the difference in volume of the fluid system with and without the sample loop 70 engaged. The formula for volume of the sample loop calculation is:

$$V_{loop} = V_{SYS-L} - V_{SYS} \quad (3)$$

Where $V_{SYS}$ is the volume of the fluid path without the loop in the fluid path and $V_{SYS-L}$ is the volume of the fluid path with the loop in the fluid path.

In a sample injector, the device is used to assure that sample liquid is positioned in the sample loop 70 while minimizing the amount of sample used. In addition, the device allows the movement of the sample liquid to occur at optimum speed. These two objectives are accomplished using at least two liquid sources and a gas bubble as a marker. The control loop 10 sends positioning command signals 42 and fluid movement signals 38 to place a gas bubble in the fluid system and then to place a measured amount of sample liquid in the fluid system. The measured amount is selected such that when the sensor 12 detects the gas bubble, the desired amount of sample will be in the sample loop 70. The control means 10 then positions the aspirating needle 50 in a non-sample source of liquid, typically liquid phase, and then issues fluid movement command signals 38 to the fluid movement means 36 to move the fluid at the optimum speed as described above until a first signal is received.

Figure 5:
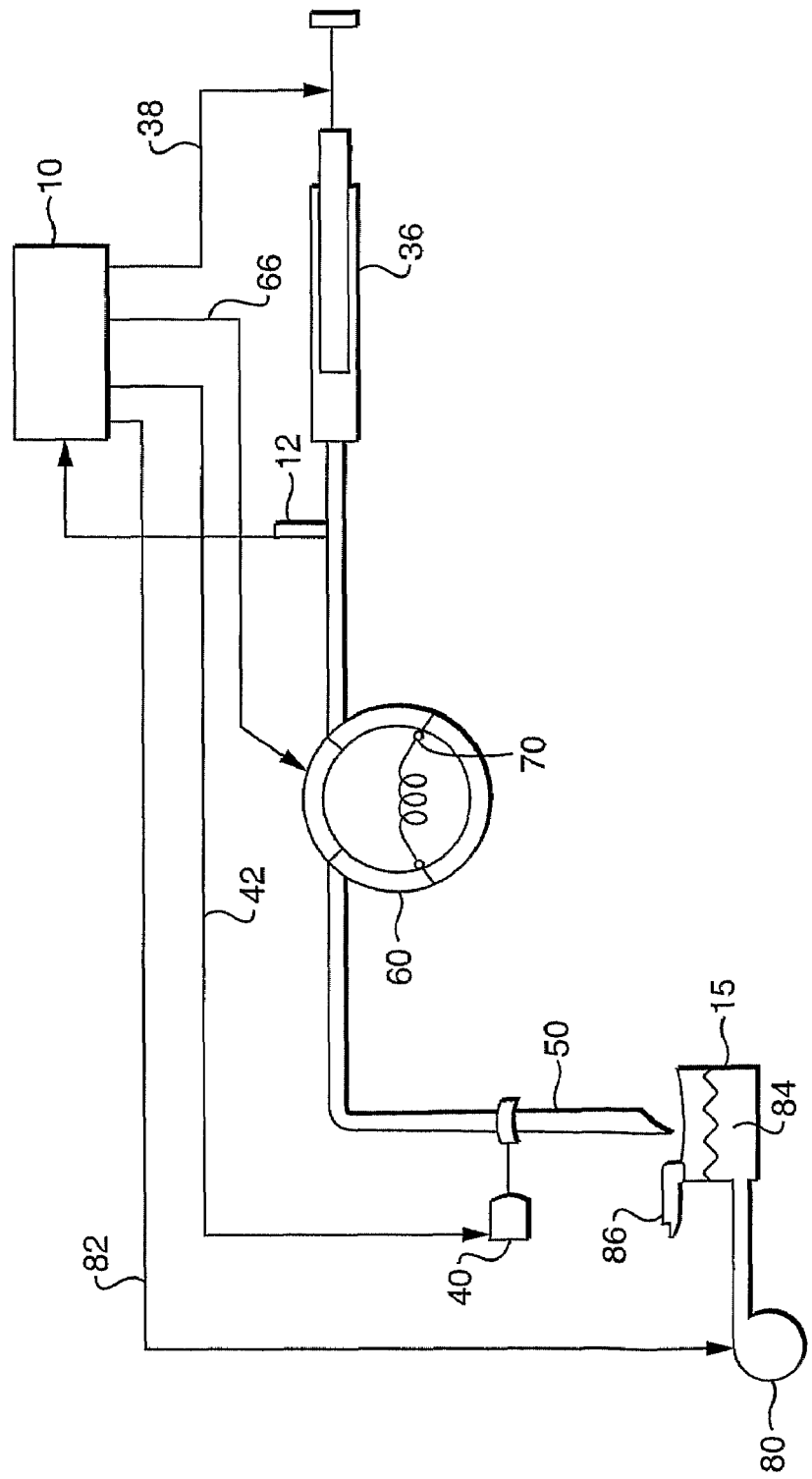
FIG. 5 illustrates the device of FIG. 1A disposed with another fluid system.

Turning now to FIG. 5, the fluid system further comprises a pressurizing means 80 connected to the source of liquid 15. The pressurizing means 80 is responsive to a pressurize command signal 82 to apply a predetermined pressure to the liquid 84 in the source of liquid 14. The control means 10 sends command signals to the positioning means 40, valve means 60, and fluid movement means 36 to form a gaseous region of a known number of aliquots of gas (an air gap) in the fluid of the fluid system. The control means further retains the aspirating needle 50 in the fluid 84 and sends a pressurize command 82 to the pressurizing means 80 to apply a predetermined pressure on the fluid system. The control means 10 immediately measures the pressurized volume of fluid ahead of the gaseous region by drawing the fluid toward the sensor 12 at the speed that would be used in positioning a sample. This pressurized volume will be smaller than the volume at ambient pressure because of a fluid transfer volume and because of a compliance volume.

$$V_{SYS} - V_{SYS-P1} = V_C + V_{FT} = V_{CR} \quad (4)$$

Where $V_{SYS}$ is the volume of the system at ambient, $V_{SYS-P1}$ is the volume of the system at the higher pressure P1 and $V_{CR}$ is the compliance rate volume. The fluid transfer volume $V_{FT}$ is the volume of fluid that is retarded by its proximity to the walls of the fluid path. The air gap passes by this fluid which is therefore not recorded as part of the pressurized volume of the fluid path. The compliance volume is the volume of spaces internal to the fluid path that open up under pressure and retain some liquid rather than allowing that liquid to be measured as part of the pressurized volume. Some compliance volume for instance is retained in the valve means. The total of compliance volume $V_C$ and fluid transfer volume $V_{FT}$ is referred to as compliance rate volume $V_{CR}$.

After the pressurized volume of the system is determined, a leakage rate is determined. The control means 10 sends command signals to the positioning means 40, valve means 60, and fluid movement means 36 to form a gaseous region of a known number of aliquots of gas (an air gap) in the fluid of the fluid system. The control means further retains the aspirating needle 50 in the fluid 84 and sends a pressurize command 82 to the pressurizing means 80 to apply a predetermined pressure on the fluid system. The control means holds the fluid system at the elevated pressure for a predetermined length of time. If the volume of the liquid in front of the gas decreases while the fluid system is held at the elevated pressure this is indicative of a leak in the fluid system. The formula for the leak rate is:

$$-LR = [(V_{SYS-P1} - V_{SYS-P2}) - V_{CR}] / \left(\frac{t_{P1-P2}}{60}\right) \quad (5)$$

WHERE $V_{SYS-P1}$ is the volume of the fluid at pressure P1, typically the ambient pressure, $V_{SYS-P2}$ is the volume of the fluid at pressure P2, $V_{CR}$ is the compliance rate volume computed above and $t_{P1-P2}$ is the time, in seconds, that the fluid was held at P2 before the second measurement.

Preferably, the fluid system further comprises a sealing means 86. The sealing means 86 is operative to seal the tip 52 of the aspirating needle 50 when the positioning means 40 positions tip 52 of the aspirating needle 50 against the sealing means 86 in response to position command signal 42. With a gaseous region of a known size in the liquid, and the aspirating needle 50 sealed by the sealing means 86, the fluid system is a closed system. The control means 10 creates a reduced pressure in the fluid system by removing some liquid from the sealed system with the fluid movement means 36. The reduced pressure allows ambient air to seep into the fluid system through any leaks present enlarging the gaseous region. The control means 10 determines a leak rate from a change in volume of the gaseous region in the fluid system after the system has been under reduced pressure for a predetermined time.

Figure 6A:
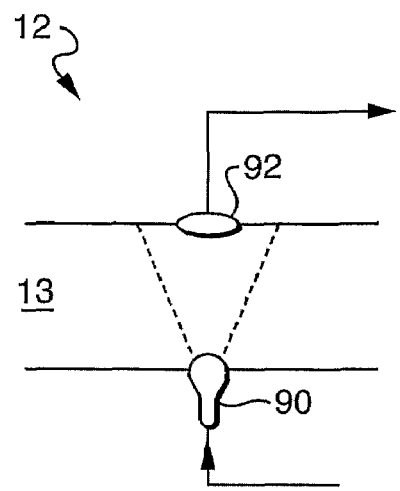
FIG. 6A illustrates an embodiment of a sensor for the device of FIG. 1A.
Figure 6B:
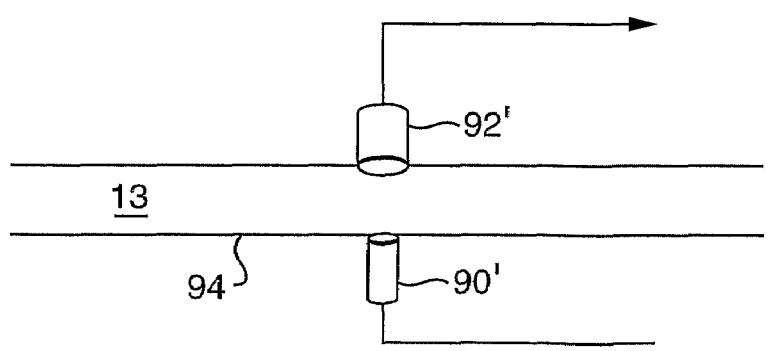
FIG. 6B illustrates a mounting for the sensor of FIG. 6A.

As shown in FIG. 6A, the sensor 12 of the device 100 preferably comprises a light emitter 90 and a light receptor 92. The light emitter 90 is constructed and arranged to emit light through the fluid 13. The light emitter 90 produces a beam of light, which, after traveling through the fluid 13, has a first characteristic when the fluid 13 is a liquid and a second characteristic when the fluid 13 is a gas. The light receptor 92 is constructed and arranged to receive light from the fluid 13. The light receptor produces the first signal 20 in response to light having the first characteristic and the second signal 22 in response to light having the second characteristic. When the control means 10 (not shown) receives these signals, typically after they have been digitized, it can distinguish between the presence of gas and liquid in the fluid system. The sensor 12 functions in a fluid system that comprises at least one vessel containing the fluid that has at least one wall with a transparent portion. The sensor 12 communicates with the fluid 13 through the transparent portion of the vessel. As shown in FIG. 6B, one implementation of the vessel is a tube 94 that is transparent. The sensor 12 is positioned so that the light emitter 90' is constructed and arranged to pass light into the tube 94 through the transparent portion and the light receptor 92' is constructed and arranged to receive light from the tube 94 through the transparent portion. Such a sensor may be used to detect bubbles.

One embodiment of the present invention is a method for monitoring moving fluid in the fluid path of a fluid system. As shown in FIG. 2, the fluid path is comprised of a fluid conduit 30 having an input end 32 and an output end 34 and a fluid movement means 36 for moving an aliquot of fluid. The fluid movement means 36 is responsive to a fluid movement command signal 38. The method comprises providing a sensor 12 and a control means 10. The sensor 12 is for placement in communication with the fluid 13 in the fluid system. The sensor 12 outputs a first signal in response to the fluid 13 being in a gaseous state and a second signal in response to the fluid 13 being in a liquid state. The control means 10 is for receiving the first signal and the second signal and for sending at least one command signal 38 for initiating a response based on the received signals. The sensor is placed in communication with the fluid 13 between the fluid movement means 36 and output end 34 of the fluid conduit. The control means 10 is connected to send a fluid movement command signal 38 to the fluid movement means 36. The control 10 means issues fluid movement command signals 38 to cause the fluid movement means 36 to draw fluid 13 in through the input end 32 at an initial rate.

Preferably, the method is used to move fluid 13 at an optimum rate that prevents vaporization. The control means 10 issues fluid movement command signals 38 to increase the rate while receiving the second signal and issues fluid movement command signals 36 to decrease the rate while receiving the first signal. When the fluid movement means is a metering syringe, each fluid movement command signal 38 draws an aliquot of fluid into the fluid conduit 30. The rate is dependent on the frequency of the fluid movement command signals, the rate increasing when the interval between signals decreases and the rate decreasing when the interval between signals increases.

Alternatively, the device is used in a method to prevent fluid 13 in a gaseous state from passing the sensor 12. The control means 10 issues fluid movement command signals 38 to cause fluid movement while receiving the second signal. The control means 10 stops issuing fluid movement command signals 38 to the fluid movement means 36 upon receiving the first signal. Therefore, the detection of the presence of gas by the sensor 12 stops further drawing of fluid 13 into the conduit.

A volume determining method to determine the volume of the fluid conduit 30 when the fluid system further comprises a positioning means 40 for moving the input end 32 between a source of liquid and a source of gas. The positioning means 40 is responsive to a position command signal 42 to move the input end 32. The position command signal 42 is connected between the control means 10 and the positioning means 40. The control means 10 commands the positioning means 40 to place the input end 32 into a source of liquid 15 and commands the fluid movement means 36 to draw at least an aliquot of liquid into the fluid conduit 30. The control means 10 then commands the positioning means 40 to place the input end 32 into a source of gas and commands the fluid movement means 36 to draw at least one aliquot of gas from the source of gas into the fluid conduit 30 forming a gas bubble. The control means 10 commands the positioning means 40 to place the input end in a source of liquid 15 and then commands the fluid movement means 36 to draw and count a plurality of aliquots of liquid from the source of liquid 15 until the first signal is received by the control means 10. This first signal indicates that the gas bubble has traversed the length of the fluid conduit 30 and the conduit 30 is filled with the counted aliquots of liquid. Then, the control means 10 determines the volume of the fluid conduit 30 by multiplying the known volume of an aliquot by the counted number of aliquots of fluid drawn and currently filling the fluid conduit 30, as illustrated in Equation (1).

Alternatively, the control means 10 determines the volume of the fluid path by commanding the fluid system that has a fluid path full of liquid to draw aliquots of gas from the source of gas until the first signal is received. By counting the aliquots moved, the control means 10 determines the volume of the fluid path in the same manner as described above.

The volume determining method is used for detecting an obstruction in the fluid path. An obstruction reduces the volume of the fluid path. The control means 10 retains initial and prior measured volumes to compare against the most currently measured volume of the fluid conduit 30. The control means 10 identifies an obstruction when the measured volume is less than a control value that depends on the retained values. The obstruction detecting method above may be used to find an obstruction in the fluid path even as further components, such as valves and needles, are added to the fluid path.

Preferably, the fluid system further comprises an aspirating needle 50 connected to the input end 32. The volume determining method is used to determine the volume of the fluid path composed of the aspirating needle 50 and the fluid conduit 30 combination. When the fluid system comprises a valve means 60 disposed between the aspirating needle 50 and the input end 32, as shown in FIG. 4, the method determines the volume of the fluid path composed of the aspirating needle 50, fluid conduit 30 and valve means 60 combination. A valve means 60 is connected into the fluid system with one port 62 connected to the aspirating needle 50 and a second port 64 connected to the input end 32 of the fluid conduit 30. The valve means 60 has a first open position, shown as a dashed connection in FIG. 4, wherein fluid is allowed to flow between the two ports 62, 64 of the valve means 60. The valve means 60 is responsive to a valve command signal 66 to assume a position. Typically valve means 60 has an accurately reported valve volume, $V_{IV}$. The method to determine the volume of the aspirating needle 50 is modified when a valve means 60 is in the fluid path to subtract both the valve volume $V_{IV}$ and the fluid conduit volume $V_{BT}$ from the fluid path volume.

The volume determining method is applicable to a fluid system that further comprises a sample loop 70 in communication with two further ports 72, 74 of the valve means 60. The valve means 60 further has a loop position, illustrated by solid lines in the valve means 60 of FIG. 4, wherein fluid is allowed to flow from the first port 62 to the second port 64 through the valve means 60 and through the sample loop 70. The valve means 60 is further responsive to the valve command signal 66 to assume the loop position. The volume determining method is further applied to determine the volume of the sample loop 70. Here, the control means 10 determines an open position volume of the fluid path, $V_{SYS}$ where the fluid path comprises the fluid conduit 30, the valve means 60 in the open position and the aspirating needle 50. Then, the control means 10 determines a loop position volume of the fluid path $V_{SYS-L}$ where the fluid path comprises the fluid conduit 30, the valve means 60 in the loop position and the aspirating needle 50. Finally, the control means 10 determines the loop volume $V_{LOOP}$ by subtracting the open position volume from the loop position volume.

The device is used in a method to position liquid, preferably sample liquid, in the sample loop 70. Because in many applications, the quantity of sample is extremely limited, it is desirable to place sample liquid in the sample loop only and fill the remainder of the fluid system with another liquid such as eluent. When there is sufficient sample fluid, the control means 10 uses a gas bubble as a marker to denote the start of the sample liquid. The control means 10 signals the valve means 60 to assume the loop position and then positions the tip 52 of the aspirating needle 50 in a source of gas. The control means signals the fluid movement means 36 to draw at least an aliquot of gas from the source of gas into the fluid system. The control means 10 then signals the positioning means 40 to move the tip 52 of the aspirating needle 50 to a source of fluid 15 and draws a plurality of aliquots of liquid from the source of liquid until the first signal is received by the control means 10. This method fills the sample loop 70 with sample, and has sample extend beyond the limits of the sample loop 70.

However, when conservation of sample is desired, the liquid can be drawn from multiple, typically two, sources in a variety of sequences that depend on how much sample is to be used. The gas bubble can be followed by a measured quantity of leader liquid, say eluent. The amount of leader liquid is typically selected to be less than the volume of the fluid conduit 30 between the valve port 64 and the sensor 12. This leader fluid is followed by a quantity of sample fluid sufficient to place a planned quantity of sample in the sample loop 70. The sample fluid is followed by a quantity of trailer liquid, again likely eluent, sufficient to fill the remainder of the fluid path. The method that conserves sample fluid requires more positioning steps as the aspirating needle 50 is moved between fluid sources, but balances these steps with the saved sample liquid.

Preferably, the fluid system further comprises a pressurizing means 80 that is responsive to a pressurize command signal 82 to apply a predetermined pressure on a source of liquid 15. The control means 10 can exercise the previously described methods under pressure, thereby moving the liquid more quickly.

The control means 10 uses the pressurizing means in a method to determine the pressurized volume of the fluid path. The control means 10 sends command signals to the positioning means 40, valve means 60, and fluid movement means 36 to form a gaseous region of a known number of aliquots of gas (an air gap) in the fluid of the fluid system. The control means further retains the aspirating needle 50 in the fluid 84 and sends a pressurize command 82 to the pressurizing means 80 to apply a predetermined pressure on the fluid system. The control means 10 immediately measures the pressurized volume of fluid ahead of the gaseous region by drawing the fluid toward the sensor 12 at the speed that would be used in positioning a sample. This pressurized volume will be smaller than the volume at ambient pressure because of a fluid transfer volume and because of a compliance volume. The fluid transfer volume $V_{FT}$ is the volume of fluid that is retarded by its proximity to the walls of the fluid path. The air gap passes by this fluid which is therefore not recorded as part of the pressurized volume of the fluid path. The compliance volume is the volume of spaces internal to the fluid path that open up under pressure and retain some liquid rather than allowing that liquid to be measured as part of the pressurized volume. The total of compliance volume $V_C$ and fluid transfer volume $V_{FT}$ is referred to as compliance rate volume $V_{CR}$, see Equation 4.

After measuring the compliance rate volume, the control means 10 determines whether a leak is present and determines a leak rate. The control means 10 positions the tip 52 of the aspirating needle 50 in a liquid source and fills the fluid system with liquid. The control means 10 repositions the tip 52 of the aspirating needle 50 to a source of gas, and draws a predetermined volume of gas into the fluid system forming a gas bubble at the tip 52 of the aspirating needle 50. The control means 10 then positions the tip 52 of the aspirating needle in the source of liquid and signals the pressurizing means 80 to apply an elevated pressure to the liquid source 84.

While under elevated pressure, any leaks will cause fluid ahead of the gas bubble to be expelled from the fluid path and replacement fluid to be drawn into the aspirating needle behind the gas bubble. The control means 10 waits a predetermined length of time before measuring the volume of liquid ahead of the gas bubble. After comparing the measured pressurized volume to the previously measured ambient volume minus the compliance rate volume, the control means 10 determines the leak rate as the change in volume over the predetermined time, see Equation 5.

When a sealing means 86 is part of the fluid system, a second method of measuring the leak rate can be utilized. The sealing means is 86 operative to seal the input end 32 (or tip 52 of the aspirating needle 50) when the positioning means 40 positions the input end 32 against the sealing means 86. In the method, the control means 10 draws a predetermined plurality of aliquots of gas into the fluid path. The control means 10 draws liquid into the fluid system until the first signal is received, indicating the leading edge of the gas bubble is at the sensor. The control means 10 then expels a predetermined number of aliquots of liquid from the fluid path to position the gas bubble at a location in the fluid system. The control means 10 then seals the input end 32 against the sealing means 86. When a number of aliquots of liquid are drawn from the system by the fluid movement means 36 under control of the control means 10, a negative pressure is created. The control means 10 maintains the system at the negative pressure for a predetermined length of time. Any increase in the volume of the gas bubble measured after a return to ambient pressure is indicative of a leak that has a calculable leak rate. The change in the volume of the gas bubble may be measured by determining a change in the volume of fluid between the leading edge of the gas bubble and the sensor, or from direct measurement of the edges of the gas bubble.

The methods above are well adapted to a device in which the sensor 12 comprises a light emitter 90 and a light receptor 92. The light emitter 90 is constructed and arranged to emit light through the fluid 13. The light emitter 90 produces a beam of light, which, after traveling through the fluid 13, has a first characteristic in the presence of a liquid and a second characteristic in the presence of a gas. The light receptor 92 is constructed and arranged to receive light from the fluid 13. The light receptor 92 produces the first signal in response to light having the first characteristic and the second signal in response to light having the second characteristic. When the control means 10 receives these signals, it may distinguish the presence of gas or liquid in the fluid system. The device sensor 12 functions in a fluid system that comprises at least one vessel containing the fluid 13 that has at least one wall with a transparent portion. The sensor 12 communicates with the fluid 13 through the transparent portion of the vessel. One implementation of the vessel is a tube 94 that is transparent. The sensor 12 is positioned so that the light emitter 90' is constructed and arranged to pass light into the tube 94 through the transparent portion and the light receptor 92' is constructed and arranged to receive light from the tube 94 through the transparent portion. Such a sensor may be used as a bubble detector. The sensor 12 is applicable to a fluid system such as a liquid chromatography system and an injector for a liquid chromatography system.

Example of Using Device for Accurate Placement of Samples in a Sample Loop

Figure 7A:
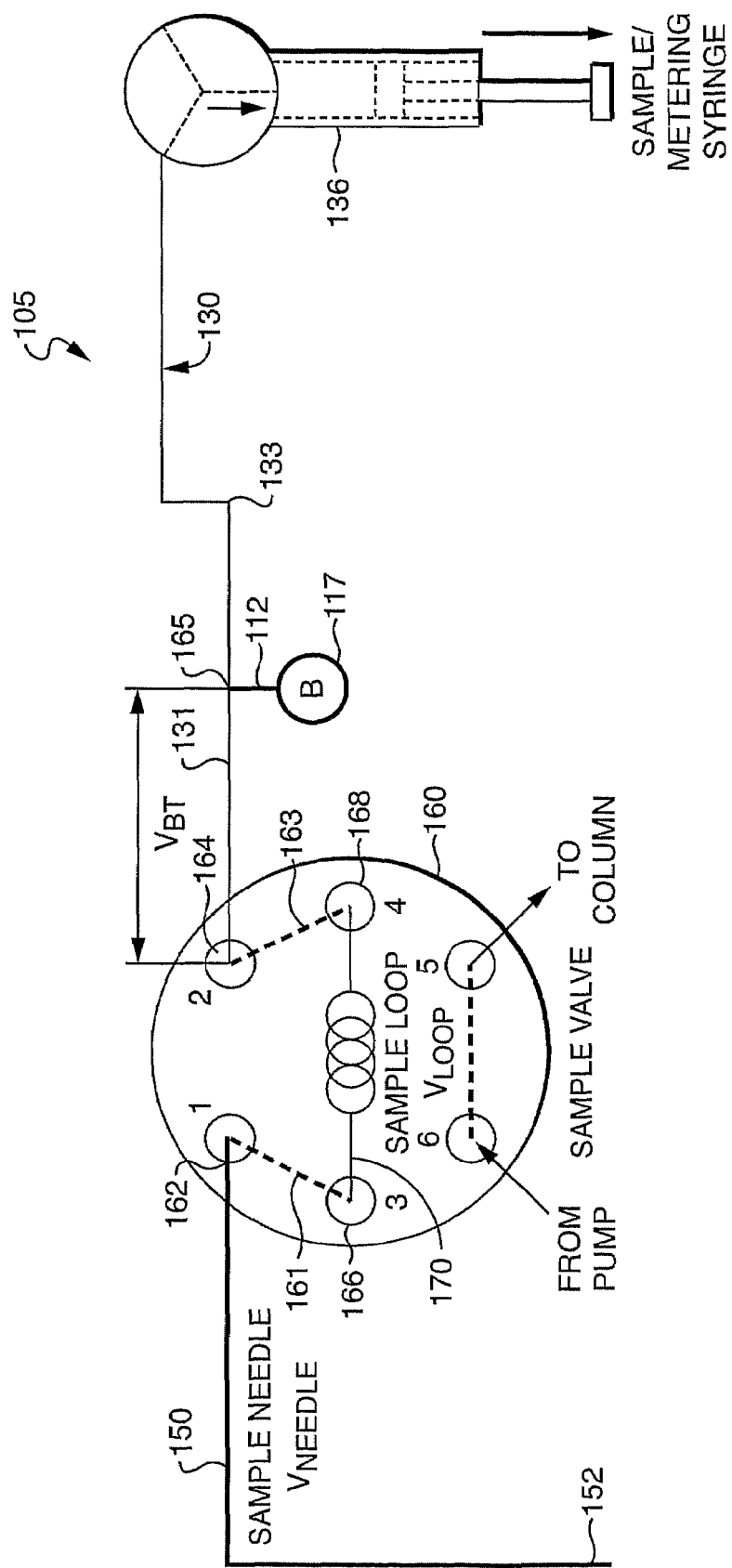
FIG. 7A illustrates the fluid path of one fluid system used in conjunction with the device of FIG. 1A.

FIG. 7A illustrates the fluid path 105 of a fluid system as used in a sample injector. The control means, positioning means, and pressurizing means of the fluid system are omitted for clarity of presentation. The injector illustrated is of the pull-to-fill type, where the sample needle tip 152 is moved between fluid sources to draw fluid into the fluid path 105. In FIG. 7A, the fluid path 105 is comprised of a sample needle 150, fluid paths 161, 163 internal to the valve means 160, a sample loop 170, a fluid conduit 130 made up of two parts—the part 131 before bubble detector 112 and the part 133 after the bubble detector 117, and the fluid movement means implemented as a metering syringe 136. Using the volume measuring method previously described above, the control means determines the volume of the fluid path with sample loop $V_{SYS-L}$ between the tip 152 of the sample needle 150 and the bubble detector monitoring point 135.

Figure 7B:
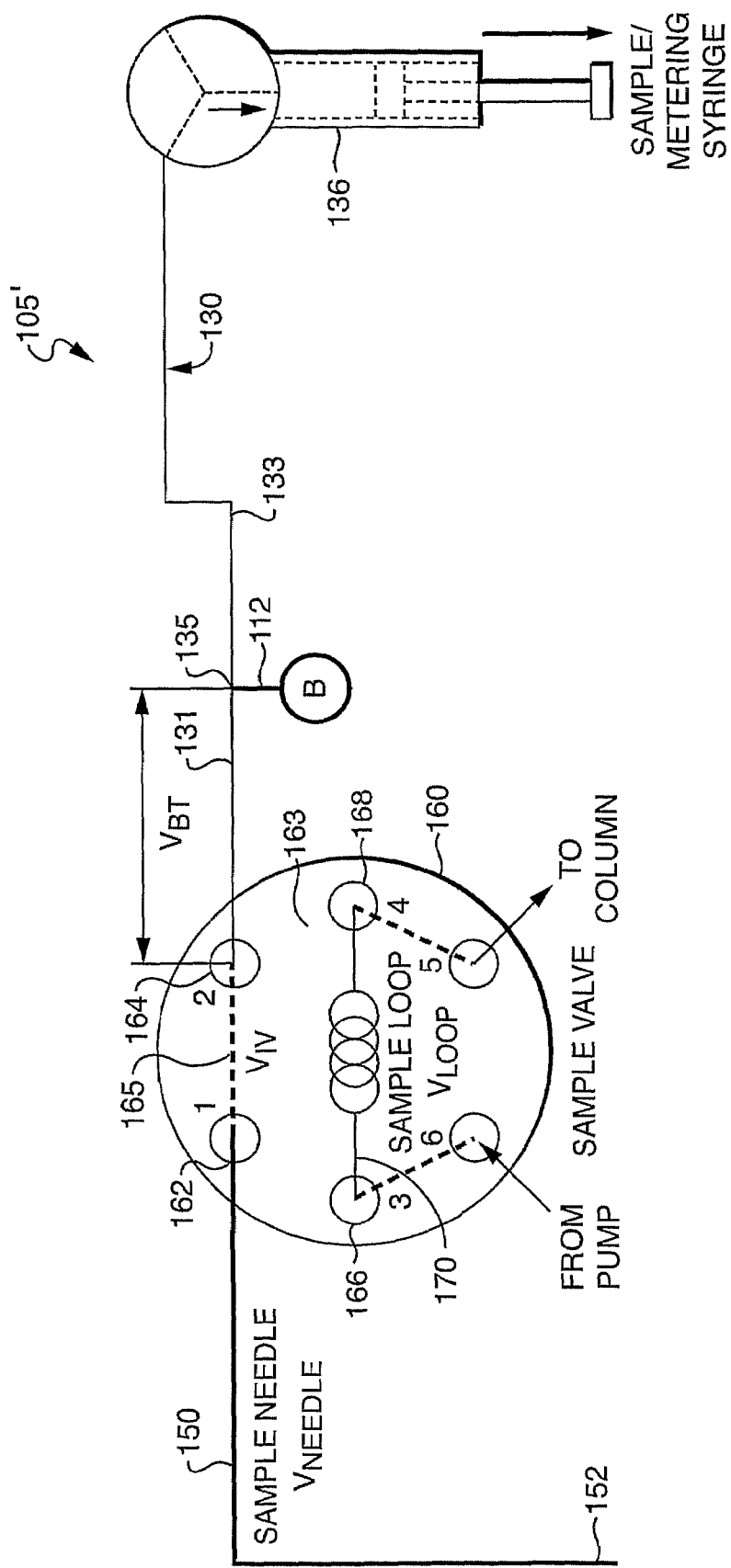
FIG. 7B illustrates another configuration of the fluid path of FIG. 7A.

FIG. 7B illustrates the fluid path 105' after the control means has changed the valve means 160 to the open position. The control means uses the volume measuring method to determine the volume of the fluid path without the sample loop $V_{SYS}$. The difference between these volumes is the loop volume $V_{LOOP}$. Prior to construction of the above fluid path 105', the volume $V_{BT}$ of the fluid conduit 131 and the volume $V_{IV}$ of the internal paths 161, 163, 165 were determined. Therefore the control means determines the volume of the sample needle as $V_{NEEDLE}=V_{SYS}-V_{IV}-V_{BT}$.

The injector system of FIG. 7 maintains the fluid path 105 full of liquid except for gaseous regions that bracket the sample. The gaseous regions maintain the concentration of the sample and aid in the sample placement under pressure. This system uses the sensor during set up and after every component replacement to determine the volumes of the sample loop and the needle. The control means knows the volume of the fluid drawn into the fluid path because the metering syringe quantifies the drawing. The sensor is used to maximize flow rate while moving the samples. The measured volumes are used to determine exactly how many aliquots of fluid need to be drawn into the fluid path to position the sample correctly.

Figure 8:
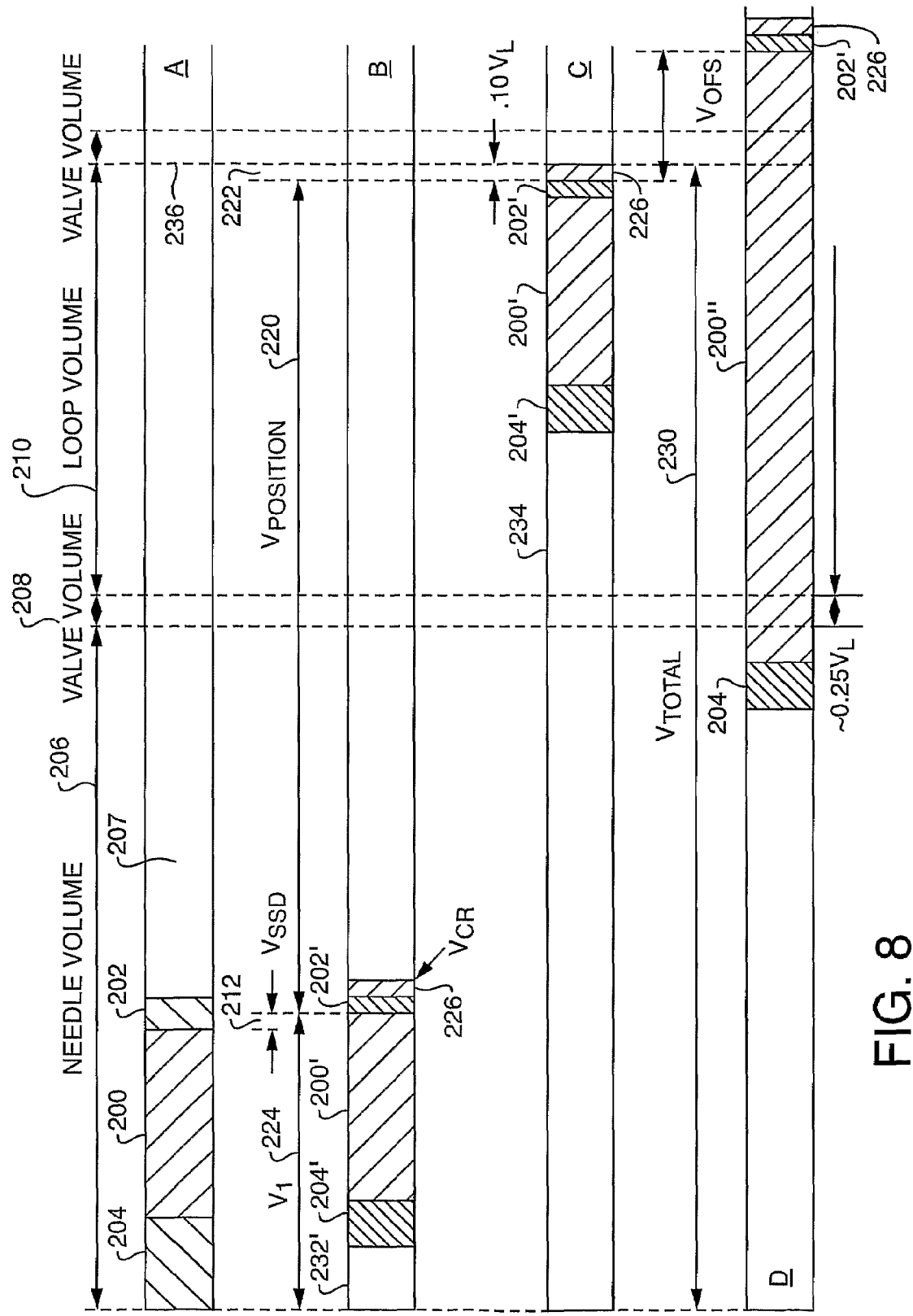
FIGS. 8A, B, C & D illustrate the use of measured volumes in a fluid path to determine the distance to move a sample.

Turning to FIG. 8A, the fluid path of FIG. 7A is displayed emphasizing the volumes of the fluid in the fluid path. A volume of sample $V_S$ (200) in the needle is to be positioned in the sample loop 210 having a sample loop volume $V_L$. The sample is bracketed by a leading air gap having a volume of $V_{AGPre}$ and a trailing air gap having a volume $V_{AGPost}$. By convention for this example, when the sample volume $V_S$ is less than or equal to 1.15 times the volume of the sample loop $V_L$, the leading edge of the leading air gap is placed in the sample loop with $\frac{1}{10}^{th}$ of the volume of the loop in front of it. Any excess sample overflows into the valve and needle. If $V_S$ is greater than $1.15V_L$, any sample beyond the $1.15V_L$ is positioned in the fluid path in front of the sample loop toward the sensor. The loop volume $V_L$ (210), valve volume $V_{IV}$ (208) and a significant portion 207 of the needle volume $V_N$ (206) is filled with liquid phase before positioning. The remainder of the needle is filled with the leader air gap 202, the sample 200 and the trailer air gap 204. The control means knows the volume of the sample $V_S$ and air gaps $V_{AGPre}$, $V_{AGPost}$ because they have been drawn in by the metering syringe 136.

FIG. 8B illustrates the fluid path after the control means has placed the path under pressure. The air gaps 202', 204' have compressed in accordance with the ideal gas law, ($V_{AGPre}'=V_{AGPre} \cdot A_{CompF}$ where $A_{CompF}$ is Air Compression Factor from the Ideal Gas Law), moving the leading edge of the sample by a volume $V_{SSD}$. Pressurized liquid phase has filled in behind the compressed trailing air gap. In addition, the system accounts for the compliance rate volume $V_{CR}$ that will be lost during positioning by regarding the air gap as having moved ahead by that volume. The control means determines the volume $V_{Position}$ that must be displaced in order to place the leading edge of the leading air gap at a distance 222 10% behind the leading end of the sample loop. It calculates $V_{Position}$ using equation (6) where $V_{OFS}$ is zero for $V_S \leq 1.15 V_L$, $$V_{Position} = V_{Total} - V_1 - .10 V_L - V_{CR} + V_{OFS} \quad (6)$$

$$V_{Total} = V_L + V_V + V_N \quad (7)$$

$$V_1 = V_S + V_{AGPost} + V_{SSD} \quad (8)$$

$V_{TOTAL}$ (230) comprises the total volume of the fluid path as expressed by equation (7), $V_1$ (224) is the volume behind the leading air gap as expressed by equation (8) where $V_S$ is the volume of the sample, and $V_{SSD}$ (212) is the displaced volume due to compression of the leading air gap and $V_{AGPost}$ is the volume of the trailing air gap before compression, $0.10 V_L$ (222) is one tenth of the volume of the sample loop, $V_{CR}$ (226) is the compliance rate volume and $V_{OFS}$ is the offset volume for full loop mode. The $V_{Position}$ volume may also be expressed as shown in equation (9).

$$V_{Position} = V_L + V_V + V_N - V_{AGPost} - V_S - V_{AGPre}*(1 - A_{Compf}) - 0.10 V_L - V_{CR} \quad (9)$$

The device moves this volume as quickly as the vapor pressure of the liquid phase and sample allow. The sensor monitors for vaporization of the fluid to maintain this optimum speed.

FIG. 8C shows the sample 200' after positioning, partially filling the sample loop. The leading edge of the leading air gap 202' is 10% of the sample loop away from the end of the sample loop 210. The volume 234 behind the trailing air gap 204' is filled with liquid phase.

In this example, when the volume of the sample $V_S$ exceeds 1.15 times the volume of the sample loop $V_L$, the sample is allowed to overlap the forward edge 236 of the sample loop 210 as illustrated in FIG. 8D. The amount of overlap is the offset volume $V_{OFS}$ and is calculated as:

$$V_{OFS} = V_S - 1.15 V_L \quad (10)$$

Using this value, the volume of fluid to be displaced is expressed as in equation (11).

$$V_{Position} = V_L + V_V + V_N - V_{AGPost} - V_{AGPre}*(1 - A_{Compf}) - 1.25 V_L - V_{CR} \quad (11)$$

Similar algorithms for positioning a sample for either partial filling or overfilling of a the sample loop can be developed using different conventions as to where to place the standard feature of the sample. Each of these will benefit from the precise measurement of the volume of the components that make up the fluid path.

Those skilled in the art will recognize, or be able to ascertain using no more than routine experimentation, numerous equivalents to the specific procedures, embodiments, claims and examples described herein. Such equivalents were considered to be within the scope of this invention and covered buy the claims appended hereto. The contents of all references, issued patents, and published patent applications cited throughout this application are hereby incorporated by reference. The invention is further illustrated by the following examples, which should not be construed as further limiting.

One skilled in the art will appreciate further features and advantages of the invention based on the above-described embodiments. Accordingly, the invention is not to be limited by what has been particularly shown and described, except as indicated by the appended claims.

What is claimed is:

1. A device for identifying a condition in a fluid system and initiating a response, the fluid system comprising a fluid conduit having an input end and an output end connected to a fluid movement means for moving an aliquot of fluid, said fluid movement means responsive to a fluid movement command signal, said device comprising:
a sensor for placement in communication with a fluid in said fluid system and disposed between said fluid movement means and said output end, said sensor outputting a first signal in response to said fluid in a gaseous state and a second signal in response to said fluid in a liquid state; and
a control means for receiving said first signal and said second signal, for issuing at least one command signal in response to the condition, for sending at least one command signal for initiating a response based on said received signals, and for issuing at least one fluid movement command signal for causing said fluid movement means to draw fluid in through said input end at a rate,
wherein said sensor and control means are placed in said fluid system, and
wherein said control means issues at least one fluid movement command signal for increasing said rate while receiving said second signal and at least one fluid movement command signal for decreasing said rate while receiving said first signal, wherein said fluid is moved at an optimum rate that prevents vaporization of said fluid.

2. The device of claim 1 wherein said fluid movement means is a metering syringe.

3. The device of claim 1 wherein said fluid system comprises a liquid chromatography system.

4. The device of claim 3 wherein said fluid system comprises an injector for a liquid chromatography system.

5. The device of claim 1 wherein said sensor comprises:
a light emitter constructed and arranged to emit light through said fluid, said light emitter producing a beam of light, which beam of light, after traveling through said fluid has a first characteristic in the presence of a liquid and a second characteristic in the presence of a gas; and
a light receptor constructed and arranged to receive light from said fluid, said light receptor producing said first signal in response to light having said first characteristic and said second signal in response to light having said second characteristic, wherein said control means may distinguish the presence of said gas or said liquid in said fluid system.

6. The device of claim 5 wherein said fluid system comprises at least one vessel for containing said fluid, said vessel having at least one wall having a transparent portion, said sensor communicating with said fluid through said transparent portion of said vessel.

7. The device of claim 6 wherein said vessel is a tube.

8. The device of claim 7 wherein said tube is transparent.

9. The device of claim 8 wherein said light emitter is constructed and arranged to pass light into said tube through said at least one transparent portion and said light receptor is constructed and arranged to receive light from said tube through said at least one transparent portion.

10. The device of claim 8 wherein said sensor is a bubble detector.

11. The device of claim 1 wherein said fluid system further comprises a positioning means for moving said input end between at least one source of liquid and at least one source of gas, said positioning means responsive to a position command signal to move said input end.

12. The device of claim 11 wherein said control means issues at least one fluid movement and position command signal for causing said fluid system to draw aliquots of liquid from said at least one source of liquid into said fluid system to fill said fluid system with liquid and then for causing said fluid system to draw and count a plurality of aliquots of gas from said at least one source of gas into said fluid system until said first signal is received by said control means.

13. The device of claim 12 wherein said control means multiplies the volume of each aliquot by said counted number of aliquots of gas drawn into said fluid system to determine a volume of said fluid conduit.

14. The device of claim 11 wherein said control means issues at least one fluid movement and position command signal for causing said fluid system to draw an aliquot of gas from said at least one source of gas into said fluid system and then for causing said fluid system to draw and count a plurality of aliquots of liquid from said at least one source of liquid into said fluid system until said first signal is received by said control means.

15. The device of claim 14 wherein said fluid system further comprises a sealing means, said sealing means operative to seal said input end when said positioning means positions said input end against said sealing means in response to at least one position command from said control means.

16. The device of claim 15 wherein said control means determines a leak rate of said fluid system, by sending at least one said position command and said fluid movement command signal to control said positioning means and said fluid movement means in conjunction with receiving said first signal and said second signal to form a gaseous region comprising a predetermined number of aliquots of gas surrounded by liquid and to determine a change in the volume of said gaseous region when said fluid system is maintained under less than ambient pressure for a predetermined length of time and then returned to said ambient pressure.

17. The device of claim 14 wherein said control means multiplies the volume of each aliquot by said counted number of aliquots of liquid drawn into said fluid system to determine a volume of said fluid conduit.

18. The device of claim 17 wherein said control means determines said volume of said fluid conduit and compares said volume to a control value to detect a reduction in said volume of said fluid conduit.

19. The device of claim 18 wherein said control value is a previous value of said volume.

20. The device of claim 19 wherein said control value is an average of previous values of said volume.

21. The device of claim 17 wherein said fluid system further comprises an aspirating needle connected to said input end.

22. The device of claim 21 wherein said fluid system further comprises a pressurizing means connected to said source of liquid, said pressurizing means responsive to a pressurize command signal to apply a predetermined pressure on said source of liquid.

23. The device of claim 21 wherein said control means determines a compliance rate volume of said fluid system by sending at least one said position command, said valve command, said pressurize command, and said fluid movement command signals to control said positioning means, said valve means, said pressurizing means, and said fluid movement means in conjunction with receiving said first signal and said second signal to determine a difference in an ambient volume of said fluid path when said fluid in said fluid path is under ambient pressure and a pressurized volume of said fluid path when said fluid in said fluid path is under an elevated pressure.

24. The device of claim 23 wherein said control means determines a leak rate by sending at least one said position command, said valve command, said pressurize command and said fluid movement command signal to control said positioning means, said valve means, said pressurizing means and said fluid movement means in conjunction with receiving said first signal and said second signal to form a gaseous region comprising aliquots of gas preceded by a computed volume of liquid between said gaseous region and said device and to determine a change in said pressurized volume of said fluid system after said fluid system is maintained at an elevated pressure for a predetermined length of time.

25. The device of claim 21 wherein said fluid system has a fluid path comprising a valve means disposed between said aspirating needle and said input end, said valve means having a plurality of positions wherein fluid is allowed to flow through said valve means, said valve means responsive to a valve command signal to assume one of said positions.

26. The device of claim 25 wherein said control means sends at least one fluid movement command, valve command and position command signal to control said fluid movement means, said valve means, and said positioning means in conjunction with receiving said first signal and said second signal to determine a needled volume of said fluid path.

27. The device of claim 26 wherein said valve means has a valve volume and said control means determines a volume of said aspirating needle by subtracting said volume of said fluid conduit and said valve volume from said needled volume of said fluid path.

28. The device of claim 25 further comprising a sample loop in communication with said valve means in said fluid path and a source of sample liquid as one of said at least one source of liquid.

29. The device of claim 28 wherein said valve means further has a loop position wherein fluid is allowed to flow through said sample loop and through said valve means, said valve means further responsive to said valve command signal to assume said loop position.

30. The device of claim 29 wherein said control means sends at least one said position command, said valve command and said fluid movement command signal to said positioning means, said valve means and said fluid movement means in conjunction with receipt of said first signal and said second signal to pull an aliquot of gas and multiple aliquots of sample liquid sequentially through said aspirating needle into said sample loop and ceases sending said fluid movement command signals when said first signal is received by said control means.

31. The device of claim 30 wherein said control means determines a volume of fluid in said sample loop by determining an open volume of said fluid path with said valve in said open position and then determining a loop volume of said fluid path with said valve in said loop position and subtracting said open volume from said loop volume.

32. The device of claim 31 wherein said control means determines a volume of fluid to displace from said fluid path in order to position a sample having a known sample volume and located at the tip of said needle to a predetermined location in said sample loop, the determination conducted by subtracting said sample volume and an offset representing said predetermined location from said volume of said fluid path comprised of said sample loop, said valve means in said loop position and said needle.

33. The device of claim 32 wherein said control means determination includes factors related to pressurization and sample location in said needle.

34. A liquid-chromatography system, comprising:
a sensor for monitoring for vaporization of a fluid moving in a pathway of the system, and for outputting first and second signals respectively associated with gaseous and liquid phases of the moving fluid;
a fluid movement means for drawing the fluid through the pathway at a rate; and
a control means for issuing, to the fluid movement means, at least one fluid movement command signal for increasing the rate in response to receipt of the second signal and at least one fluid movement command signal for decreasing the rate in response to receipt of the first signal to cause the fluid movement means to draw the fluid at an optimum rate that prevents vaporization of the fluid.

* * * * *